(12) United States Patent
Bunke et al.

(10) Patent No.: US 7,287,557 B2
(45) Date of Patent: Oct. 30, 2007

(54) ANESTHETIC TANK OF AN ANESTHETIC DISPENSING UNIT

(75) Inventors: Claus Bunke, Sereetz (DE); Matthias Witt, Bad Schwartau (DE); Rainer Kunz, Lübeck (DE); Jürgen Müller, Lübeck (DE); Sven Heyer, Lübeck (DE); Dirk Reichert, Lübeck (DE); Henryk Schnaars, Lübeck (DE); Michael Heidschmidt, Lübeck (DE); Martin Wunderlich, Lübeck (DE); Ralf Dittmann, Blankensee (DE)

(73) Assignee: Dräger Medical AG & Co. KGaA (DE)

( * ) Notice: Subject to any disclaimer, the term of this patent is extended or adjusted under 35 U.S.C. 154(b) by 195 days.

(21) Appl. No.: 11/139,773

(22) Filed: May 27, 2005

(65) Prior Publication Data

US 2006/0042626 A1    Mar. 2, 2006

(30) Foreign Application Priority Data

Aug. 24, 2004    (DE) ................ 10 2004 040 930

(51) Int. Cl.
    *B65B 1/04*    (2006.01)
(52) U.S. Cl. ............................ 141/95; 141/198; 141/2; 141/18
(58) Field of Classification Search ............ 141/2, 141/118, 351, 94, 95, 198; 73/323, 327, 73/290 B; 222/51, 155, 157; 116/227; 128/200.14–200.23
    See application file for complete search history.

(56) References Cited

U.S. PATENT DOCUMENTS

| | | | | | |
|---|---|---|---|---|---|
| 5,470,511 A | * | 11/1995 | Laybourne et al. | ............ | 261/55 |
| 5,560,584 A | * | 10/1996 | Falb et al. | .................. | 251/89.5 |
| 5,785,100 A | * | 7/1998 | Showalter et al. | .......... | 141/198 |
| 5,918,593 A | * | 7/1999 | Loser | .................... | 128/200.16 |
| 6,012,795 A | * | 1/2000 | Saito et al. | ..................... | 347/7 |
| 6,040,776 A | * | 3/2000 | Glover et al. | ............... | 340/618 |
| 6,125,893 A | * | 10/2000 | Braatz et al. | ................. | 141/18 |
| 6,672,306 B2 | * | 1/2004 | Loser et al. | ........... | 128/203.12 |

FOREIGN PATENT DOCUMENTS

| | | |
|---|---|---|
| DE | 35 23 948 C2 | 1/1987 |
| DE | 41 06 756 A1 | 9/1992 |
| FR | 1 529 160 | 6/1967 |
| GB | 554 390 | 7/1943 |
| GB | 2 177 008 A | 1/1987 |

OTHER PUBLICATIONS

U.S. Appl. No. 11/145,863, filed Jun. 6, 2005, Bunke et al.

* cited by examiner

*Primary Examiner*—Steven O. Douglas
(74) *Attorney, Agent, or Firm*—McGlew and Tuttle, P.C.

(57) ABSTRACT

An anesthetic tank (1) of an anesthetic dispensing unit is used especially for desflurane and has improved reliability of operation by mutually complementing level monitoring devices. The anesthetic tank (1) is equipped with a level tube (3) arranged in or on the outer wall with a connection line (6) into the interior space as well as with an optical level sensor (4). The optical axis (5) of the level sensor (4) is located at the same level as a mark (33) on the level tube (3).

20 Claims, 1 Drawing Sheet

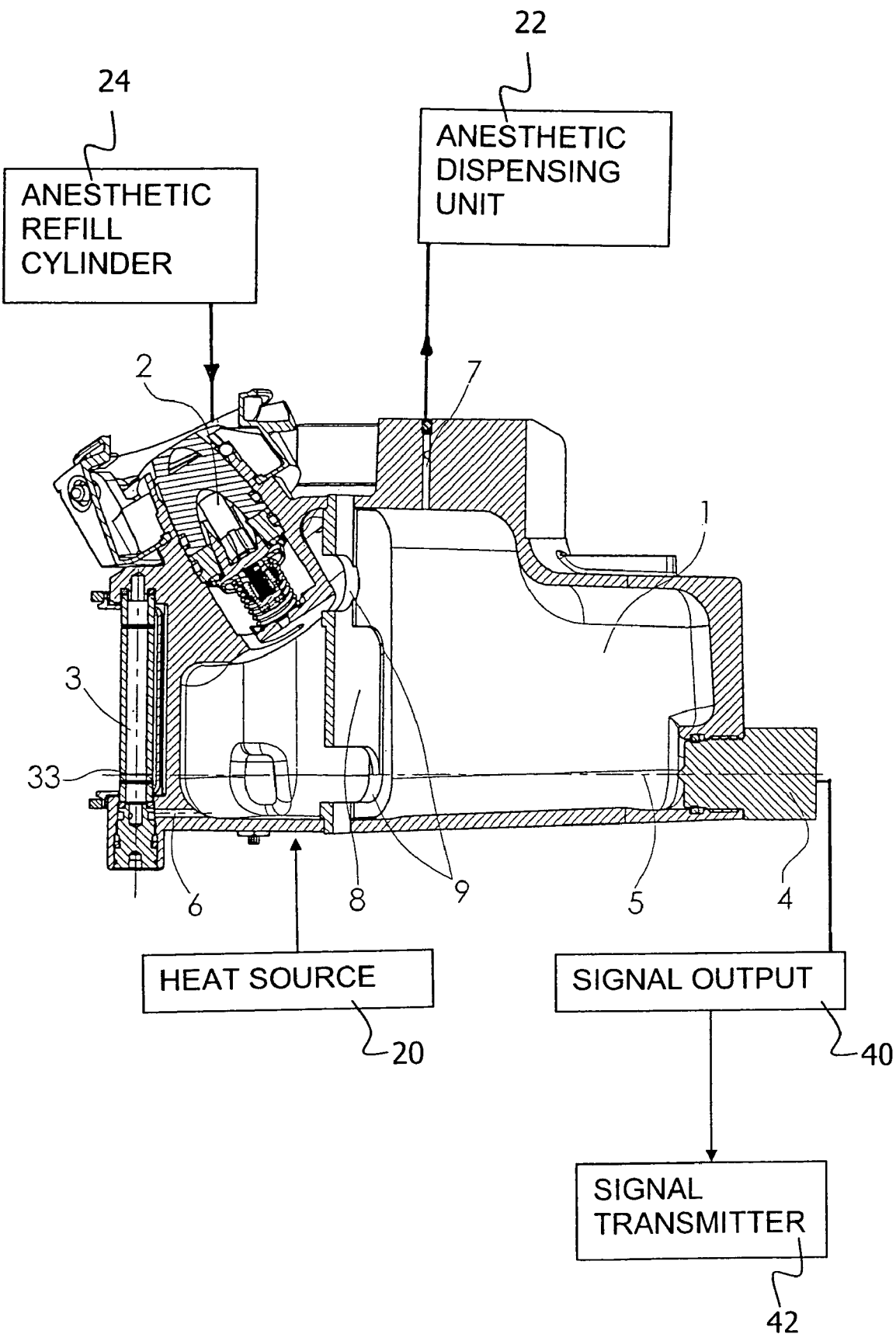

ANESTHETIC TANK OF AN ANESTHETIC DISPENSING UNIT

CROSS REFERENCE TO RELATED APPLICATIONS

This application claims the benefit of priority under 35 U.S.C. § 119 of German Application DE 10 2004 040 930.7 filed Aug. 24, 2004, the entire contents of which are incorporated herein by reference.

FIELD OF THE INVENTION

The present invention pertains to an anesthetic tank of an anesthetic dispensing unit and more particularly to such an anesthetic tank with a level tube as well as an anesthetic dispensing system and method.

BACKGROUND OF THE INVENTION

Various dispensing systems, in which the anesthetic is fed from an associated anesthetic tank, are known for dispensing anesthetics. To monitor the ability to operate uninterruptedly for dispensing anesthetics, it is, furthermore, known that a level tube, for example, one corresponding to DE 41 06 756 A1, which communicates with the interior space of the anesthetic tank, is arranged on the outer wall of the anesthetic tank, so that the level in the anesthetic tank can be read on the outside. Capacitive level sensors for such an anesthetic tank are disclosed, for example, in DE 35 23 948 C2.

SUMMARY OF THE INVENTION

The object of the present invention is to provide an anesthetic tank of an anesthetic dispensing unit as an anesthetic dispensing system and method with an anesthetic level monitoring that is improved in terms of the reliability of operation.

According to the invention an anesthetic tank, anesthetic dispensing system and anesthetic dispensing method are provided. The tank of an anesthetic dispensing unit is equipped with a level tube arranged in or on the outer wall with a connection line into the interior space as well as with an optical level sensor. An optical axis of the level sensor is located at the same level as the mark on the level tube.

The present anesthetic tank is substantially improved concerning the reliability of operation for the patient supplied with anesthetic due to the mutually complementing level monitoring means.

The level sensor may be an electro-optic digital comparator, so that the percentage of the coupled radiated power totally reflected at a prism of the level sensor, which percentage varies as a function of the anesthetic level, is an indicator of the anesthetic level.

The electric signal output of the level sensor may be connected with an optical and/or acoustic signal transmitter, especially in a wireless manner.

The level of the mark on the level tube may be selected to be such that when the corresponding level is reached by the anesthetic, the anesthetic tank can take up a refill volume corresponding to the contents of an anesthetic refill cylinder.

A partition may be arranged at right angles to the optical axis with at least one passage for the anesthetic, wherein the anesthetic tank consists of a pressure-resistant aluminum alloy.

The anesthetic used may advantageously be desflurane.

An exemplary embodiment of the present invention will be explained below on the basis of the only FIGURE. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a vertical sectional view through an anesthetic tank of an anesthetic dispensing unit according to the invention and also schematically showing anesthetic dispensing system features.

DESCRIPTION OF THE PREFERRED EMBODIMENTS

Referring to the drawings in particular, an anesthetic tank 1 of the shown example according to the invention comprises a pressure-resistant aluminum alloy for the controlled release of the relatively volatile anesthetic. The anesthetic tank 1 is preferably a heated anesthetic tank 1, heated by e.g., a heat source 20 shown schematically. The relatively volatile anesthetic is especially desflurane in the vapor form. The desflurane vapor is released through the hole 7 to a downstream anesthetic dispensing unit 22 shown schematically, which is known per se. The vertical partition 8 consisting of an aluminum alloy in the example with two passages 9 in the example is used to increase the mechanical stability of the anesthetic tank 1. The anesthetic tank 1 can be refilled with anesthetic, especially desflurane. The refilling is done by means of the filling means 2 with an inlet valve, which cooperates with an outlet valve in a corresponding refilling cylinder 24, shown schematically, which can be introduced into the filling means 2.

It is especially important for the controlled supply of a patient with anesthetic during an operation performed with anesthesia that there should be no interruption in the dispensing of the anesthetic. Timely refilling of the anesthetic tank 1 with anesthetic is an essential prerequisite for this, which is accomplished with the means being described here: Visibly from the outside, a vertical level tube 3, which is in liquid connection with the interior space of the anesthetic tank 1 by means of the connection line 6, is arranged on the anesthetic tank 1, so that the liquid level in the anesthetic tank 1 is visible from the level tube 3. In addition, the anesthetic tank 1 has an optical level sensor 4, whose optical axis 5 is located at the same level as a mark 33 on the level tube 3. The site and height of installation of the level sensor 4 with the optical axis 5 and the mark 33 are selected to be such that when the corresponding filling level is reached by the anesthetic, the anesthetic tank 1 can take up a refill volume of, for example 240 mL or 250 mL corresponding to the contents of an anesthetic refill cylinder 24, but, on the other hand, a sufficient anesthetic reserve is still present in the anesthetic tank 1 to continue dispensing the anesthetic and to perform the refilling operation without interruption. If the level drops below the mark 33, an optical and/or acoustic signal is triggered for the operating personnel by means of the electric output signal (from signal output 40) of the optical level sensor 4 and corresponding signal transmitters 42.

The optical level sensor 4 used is an electro-optical digital comparator, for example, from the company Gems Sensors Inc. The principle of measurement is based on the laws of diffraction and total reflection of the electromagnetic radiation of a diode emitting, for example, infrared light (LED), whose radiation is sent through an optical prism and totally reflects varying percentages of the radiation as a function of the anesthetic level, so that a corresponding electric output signal is sent to the optical and/or acoustic signal transmitter for an alarm via a detector present in the level sensor 4, which said detector receives the reflected radiation. The percentage of totally reflected radiation changes abruptly as soon as the environment of the level sensor 4 is no longer surrounded by liquid anesthetic, because the refractive index at the interface to the optical prism will then have changed correspondingly: The prism is adjoined by anesthetic vapor instead of liquid anesthetic.

While a specific embodiment of the invention has been shown and described in detail to illustrate the application of the principles of the invention, it will be understood that the invention may be embodied otherwise without departing from such principles.

What is claimed is:

1. An anesthetic tank of an anesthetic dispensing unit, the anesthetic tank comprising:
   an outer wall;
   a level tube arranged in or on the outer wall, the level tube having a mark, said level tube being transparent such that an operator can view anesthetic in said level tube corresponding to a level of anesthetic in the anesthetic tank;
   a connection line providing a connection from the level tube into the interior space of an adjacent anesthetic tank region, whereby anesthetic in a liquid form fills said level tube to a level corresponding to the liquid level of anesthetic in said anesthetic tank;
   an optical level sensor having an optical axis located at the same level as said mark on said level tube, whereby said mark defines a threshold amount of anesthetic remaining in the anesthetic tank, said level tube having optical characteristics, said optical characteristics changing based on the presence or absence of anesthetic in said level tube in a region of said mark, said optical level sensor detecting changes in said optical characteristics;
   an alarm means connected to said optical level sensor for activating an alarm, said alarm being activated when said optical characteristics change such that said optical level sensor detects an amount of anesthetic at or below said threshold amount.

2. An anesthetic tank in accordance with claim 1, wherein the level sensor includes an electro-optic digital comparator with a prism whereby a percentage of coupled radiated power totally reflected at the prism of the level sensor, which percentage varies as a function of the anesthetic level, is an indicator of the anesthetic level.

3. An anesthetic tank in accordance with claim 1, wherein the electric signal output of the level sensor is connected with a optical and/or acoustic signal transmitter.

4. An anesthetic tank in accordance with claim 1, wherein the level of the mark on the level tube is selected to be such that when the corresponding level is reached by the anesthetic, the anesthetic tank can take up a refill volume corresponding to the contents of an anesthetic refill cylinder.

5. An anesthetic tank in accordance with claim 1, further comprising a partition arranged at right angles to the optical axis, said partition having at least one said passage for the anesthetic, the anesthetic tank consisting essentially of a pressure-resistant aluminum alloy.

6. An anesthetic tank in accordance with claim 1, wherein the anesthetic used is desflurane.

7. An anesthetic tank in accordance with claim 1, wherein the electric signal output of the level sensor is connected with the optical and/or acoustic signal transmitter in a wireless manner.

8. An anesthetic dispensing system comprising:
   an anesthetic tank with an outer wall and mutually complementing level monitoring means for monitoring a level of anesthetic in the anesthetic tank including a level tube with an externally observable refill mark, whereby said refill mark defines a threshold amount of anesthetic remaining in said anesthetic tank, the level tube being arranged in or on the tank outer wall with a connection line into the interior space of said anesthetic tank whereby anesthetic in a liquid form fills the level tube to the same fill level as liquid anesthetic in the tank and an optical level sensor having an optical axis located at the same level as a mark on the level tube, said level tube having optical characteristics, said optical characteristics changing based on the presence or absence of anesthetic in said level tube in a region of said mark, said optical level sensor detecting changes in said optical characteristics;
   an alarm means for activating an alarm, said alarm being activated when said optical level sensor detects a level of anesthetic that is at or below said threshold amount.

9. An anesthetic dispensing system in accordance with claim 8, wherein said optical level sensor includes a prism with a prism apex at said optical axis whereby a percentage of coupled radiated power totally reflected at the prism of the level sensor, which percentage varies as a function of the anesthetic level, is an indicator of the anesthetic level.

10. An anesthetic dispensing system in accordance with claim 9, wherein the electric signal output of the level sensor is connected with a optical and/or acoustic signal transmitter.

11. An anesthetic dispensing system in accordance with claim 9, further comprising:
    an anesthetic dispensing unit connected to said anesthetic tank;
    an anesthetic refill cylinder wherein the level of the mark on the level tube is selected to be such that when the corresponding level is reached by the anesthetic, upon an amount of anesthetic passing from said tank to said anesthetic dispensing unit, said tank takes up a refill volume corresponding to the contents of said anesthetic refill cylinder.

12. An anesthetic dispensing system in accordance with claim 9, wherein said tank outer wall comprises a pressure-resistant aluminum alloy.

13. An anesthetic dispensing system in accordance with claim 12, further comprising:
    a partition arranged at right angles to the optical axis, said partition having at least one passage for the anesthetic.

14. An anesthetic dispensing system in accordance with claims 11, desflurane in liquid form is the anesthetic disposed in the tank.

15. An anesthetic dispensing method comprising:
    providing an anesthetic dispensing unit;
    providing an anesthetic tank with an outer wall defining an anesthetic space and having a vapor connection for passing vapor anesthetic to the anesthetic dispensing unit;
    providing a level tube with an externally observable mark, the level tube being arranged in or on the tank outer wall with a connection line into said anesthetic space whereby anesthetic in a liquid form fills the level tube to the same fill level as liquid anesthetic in the tank, said level tube being transparent such that an operator can view anesthetic in said level tube corresponding to a level of liquid anesthetic in said anesthetic tank;

providing an optical level sensor having an optical axis, said level tube having optical characteristics, said optical characteristics changing based on the presence or absence of anesthetic in said level tube in a region of said mark, said optical level sensor detecting changes in said optical characteristics;

locating the optical axis of the optical level sensor at the same level as said mark, whereby said mark indicates a threshold amount of anesthesia remaining in said anesthetic tank;

activating an alarm when said optical sensor detects a level of anesthetic in said tank that is at or below said threshold amount.

16. An anesthetic dispensing method in accordance with claim 15, wherein the optical level sensor includes a prism and further comprising:

indicating the anesthetic level based on a percentage of coupled radiated power totally reflected at the prism of the level sensor, which percentage varies as a function of the anesthetic level.

17. An anesthetic dispensing method in accordance with claim 16, further comprising:

connecting an electric signal output of the level sensor with a optical and/or acoustic signal transmitter.

18. An anesthetic dispensing method in accordance with claim 15, further comprising:

providing an anesthetic refill cylinder;

selecting the level of the mark on the level tube to be such that when the corresponding level is reached by the anesthetic, upon an amount of anesthetic passing from said tank to said anesthetic dispensing unit, said tank can take up a single refill volume corresponding to the contents of said anesthetic refill cylinder.

19. An anesthetic dispensing method in accordance with claim 15, further comprising: providing the outer wall as a pressure-resistant aluminum alloy; and arranging a partition at right angles to the optical axis, said partition having at least one passage for the anesthetic; and providing desflurane in liquid form as the anesthetic disposed in the tank.

20. An anesthetic dispensing method in accordance with claim 17, further comprising:

a transmitting signal wirelessly from the signal output of said optical level sensor to the optical and/or acoustic signal transmitter.

* * * * *